United States Patent [19]
Pfister

[11] 4,260,558
[45] Apr. 7, 1981

[54] PROCESS FOR THE PREPARATION OF AROMATIC AMINOHYDROXY COMPOUNDS

[75] Inventor: Theodor Pfister, Wuppertal, Fed. Rep. of Germany

[73] Assignee: Bayer Aktiengesellschaft, Leverkusen, Fed. Rep. of Germany

[21] Appl. No.: 953,805

[22] Filed: Oct. 23, 1978

[30] Foreign Application Priority Data

Nov. 16, 1977 [DE] Fed. Rep. of Germany ....... 2751136

[51] Int. Cl.³ .................... C07C 99/00; C07C 139/00; C07C 143/56; C07C 143/64
[52] U.S. Cl. ................................ 260/507 R; 260/509; 562/453; 564/428; 564/443; 564/418
[58] Field of Search .................. 260/507 R, 509, 575; 562/453

[56] References Cited

U.S. PATENT DOCUMENTS 3,359,315  12/1967  Kosak .................................. 260/575

OTHER PUBLICATIONS

Rothenberg, "Chem. Ber.," vol. 26, pp. 2060-2061 (1893).
Furst et al, "Chem. Rev.", vol. 65, pp. 51-63, (1964).
Albert, "J.A.C.S." vol. 76, pp. 4985-4988, (1954).
Weygand et al., "Prep. Org. Chem.," John Wiley & Sons, New York, 1972, 4th Edition, pp. 557-563, 566 & 567.

Primary Examiner—Norman Morgenstern
Attorney, Agent, or Firm—Sprung, Felfe, Horn, Lynch & Kramer

[57] ABSTRACT

An improvement in the process for the preparation of an aromatic hydroxy compounds by reacting an aromatic nitroso compound of the formula

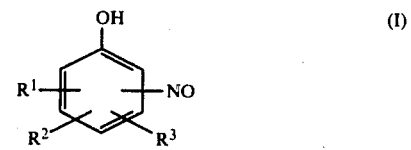

wherein
$R^1$, $R^2$ and $R^3$ independently represent hydrogen, a lower alkyl radical, halogen, a carboxyl or sulfo group or the corresponding alkali metal salt thereof or
$R^1$, $R^2$ or $R^3$ individually represent an optionally substituted aromatic ring formed by linking two adjacent radicals, with hydrazine, the improvement residing in reacting the aromatic nitroso compound with the hydrazine in approximately equivalent amounts in an aqueous medium at temperatures from 10° to 50° C., in the absence of a catalyst the aromatic nitroso compound being initially introduced into a reaction chamber and the hydrazine being added thereto.

8 Claims, No Drawings

PROCESS FOR THE PREPARATION OF AROMATIC AMINOHYDROXY COMPOUNDS

The invention relates to a process for the preparation of aromatic aminohydroxy compounds by reducing corresponding aromatic nitrosohydroxy compounds with hydrazine.

It is known to reduce 2-nitroso-5-acetyl-amino-1-naphthol to 2-amino-5-acetyl-amino-1-naphthol with phenylhydrazine without adding a catalyst (Houben-Weyl, Methoden der organischen Chemie (Methods of organic chemistry), volume XI/1, page 494 (1957)).

It is also known to react aromatic nitroso compounds, such as p-nitrosodiethylaniline, with hydrazine in the presence of Raney nickel as a catalyst and ethyl alcohol as a solvent to give the corresponding amine (Ann. Chim. (Rome) 47, 410 (1957)) and Chem. Reviews 65, 53 to 68 (1965)).

A process has been found for the preparation of aminohydroxy compounds by reacting an aromatic nitroso compound of the formula

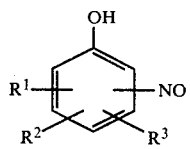

wherein $R^1$, $R^2$ and $R^3$ are identical or different and denote hydrogen, a lower alkyl radical, halogen, a carboxyl or sulpho group or an optionally substituted aromatic ring formed by linking two adjacent radicals or the corresponding alkali metal salts thereof with hydrazine, characterised in that the aromatic nitroso compound and the hydrazine are reacted in approximately equivalent amounts in an aqueous medium at temperatures from 10° to 50° C., the aromatic nitroso compound being initially introduced and the hydrazine being added. Where $R^1$, $R^2$ and $R^3$ is a carboxyl or sulpho group the corresponding salt thereof e.g. alkali metal salt can be employed as well.

The process according to the invention can be illustrated by the equation which follows which employs the sodium salt of 1-nitroso-4-hydroxy-benzene-3-sulphonic acid as the nitroso compound:

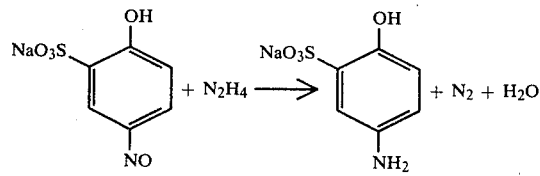

Lower alkyl radicals which may be mentioned are hydrocarbon radicals with 1 to 6 carbon atoms, such as methyl, ethyl, propyl, isopropyl, butyl, isobutyl, pentyl, isopentyl, hexyl and isohexyl. Preferred lower alkyl radicals are methyl and ethyl.

Halogens which may be mentioned are fluorine, chlorine, bromine and iodine, preferably chlorine.

The naphthalene system may preferably be mentioned as an aromatic ring system which is formed by linking two adjacent radicals. This can be optionally substituted by one or more radicals, the radicals having the same scope of meaning as $R^1$, $R^2$ and $R^3$.

Compounds of the formula

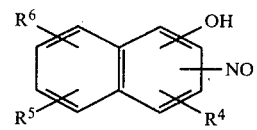

wherein $R^4$, $R^5$ and $R^6$ are identical or different and denote hydrogen or a carboxyl or sulpho group or the corresponding alkali metal-salts thereof may be mentioned as preferred aromatic nitroso compounds.

The preparation of the aromatic nitroso compounds is known (Houben-Weyl, Methoden der organischen Chemie (Methods of organic chemistry), volume X/1, page 1028–1037 (1971)) and can be carried out, for example, by reacting aromatic hydroxy compounds with nitrous acid and its derivatives.

The following aromatic nitroso compounds may be mentioned as examples: 1-nitroso-2-hydroxy-naphthalene-4-sulphonic acid, 1-nitroso-2-hydroxy-naphthalene-6-sulphonic acid, 2-nitroso-1-hydroxy-naphthalene-4-sulphonic acid, 1-nitroso-2-hydroxy-naphthalene-3,6-disulphonic acid, 1-nitroso-2-hydroxy-naphthalene, 1-nitroso-4-hydroxy-naphthalene, 2-nitroso-1-hydroxy-naphthalene, 1-nitroso-2-hydroxy-benzene, 1-nitroso-4-hydroxy-benzene, 1-nitroso-2-hydroxy-benzene-5-sulphonic acid, 1-nitroso-4-hydroxy-benzene-3-sulphonic acid and 1-nitroso-4-hydroxy-benzene-3-carboxylic acid.

One can, of course, employ hydrazine hydrate as the hydrazine for the process according to the invention. The hydrazine can be employed in concentrated and in dilute aqueous solution. In general, an aqueous hydrazine solution containing 10 to 90% by weight, preferably 20 to 80% by weight, of hydrazine is used.

The nitroso compound and the hydrazine are employed in the process according to the invention in approximately equivalent amounts. In general, 1.0 to 1.3 mols, preferably 1.05 to 1.20 mols, of hydrazine are reacted with one mol of the aromatic nitroso compound.

The process according to the invention is generally carried out in the temperature range from 10° to 50° C., preferably in the temperature range from 20° to 40° C.

The process according to the invention can be carried out under normal pressure, increased pressure or reduced pressure. In general, it is carried out under atmospheric pressure.

The process according to the invention is carried out in an aqueous medium. Moreover, it is of course also possible to use other solvents or diluents, such as alcohols, for example methanol or ethanol, or cyclic ethers, for example dioxane. Water is the preferred solvent for the process according to the invention.

The process according to the invention is in general carried out in the pH range from 4 to 14, preferably from 8 to 12. More strongly acid reaction mixtures can optionally be established by adding bases, for example sodium hydroxide solution, to a pH value of 4 to 14 before the reaction with hydrazine.

The process according to the invention can be carried out, for example, as follows:

The nitroso compound is dispersed in water and the aqueous hydrazine solution is metered in at a rate corresponding to the rate of reaction. After the reaction has ended, the reaction product can be precipitated in the customary manner, for example by acidification with hydrochloric acid, and then isolated. If necessary, further purification measures, such as recrystallisation or reprecipitation, are possible.

The rate of reaction can easily be controlled by regulating the rate of dropwise addition of the hydrazine. Since it depends on apparatus parameters, the optimum value is appropriately determined for each reaction apparatus. In general, the hydrazine can be added dropwise to the aromatic nitroso compound at a rate of 1 to 10 ml/minute.

In a preferred embodiment of the process according to the invention, the nitroso compound is dissolved or suspended in water and, after adjusting the pH value to 8 to 12 and the internal temperature to about 30° C., a 20 to 40% strength aqueous solution of hydrazine hydrate is metered in at a rate corresponding to the rate of reaction. The temperature is kept in the range from 20° to 40° C. The course of the reaction can easily be monitored by the evolution of gas.

The process according to the invention can advantageously be carried out in a simple manner with a low expenditure on apparatus. The process according to the invention can advantageously be carried out in an aqueous solution or suspension, so that there is no pollution by other solvents.

The process according to the invention can advantageously be carried out without adding metal catalysts, which are frequently necessary in hydrogenation reactions with hydrazine.

Since it is known (Houben-Weyl, Methoden der organischen Chemie (Methods of organic chemistry), volume XI/1, page 452–457 and page 490–494 (1957)) that nitroso compounds can be carried out with hydrazine either at relatively high temperatures without a catalyst or under mild conditions with the aid of a catalyst, the process according to the invention is also surprising.

Aromatic aminohydroxy compounds of the formula

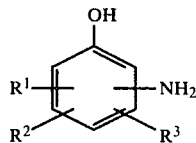

wherein $R^1$, $R^2$ and $R^3$ have the abovementioned meaning, can be prepared by the process according to the invention.

The aromatic aminohydroxy compounds which can be prepared by the process according to the invention can be used as photographic developers or as intermediate products for azo dyestuffs.

EXAMPLE 1

235 ml (1.1 mols) of a 23.5% strength aqueous solution of hydrazine hydrate are added dropwise to a suspension, warmed to 30° C., of 388 g (1.0 mol) of 1-nitroso-2-hydroxy-naphthalene-6-sulphonic acid (Na salt; 65.3% pure) in one liter of water in the course of 60 minutes at a pH value of 8 to 12, whilst stirring, the internal temperature being kept at 25° to 35° C. The mixture is stirred at the temperature indicated for about a further hour, until the evolution of gas has virtually ended. The pH value is adjusted to approximately 1 by adding 75 ml of 18% strength hydrochloric acid dropwise and 1-amino-2-hydroxy-naphthalene-6-sulphonic acid is precipitated as betaine in the form of pink-tinged crystals. After cooling with ice and stirring for a short time, the crystals are filtered off, washed with methanol and dried at 40° C. in vacuo. Yield: 210 g (88%, or 82% of theory, taking into consideration the cerimetrically determined content of 93.3%).

Calculated: C 50.2, H 3.8, N 5.9, S 13.4,
Found: C 50.4, H 4.0, N 6.3, S 13.2.

What is claimed is:

1. In a process for the preparation of an aminohydroxy compound by contacting an aromatic nitroso compound of the formula

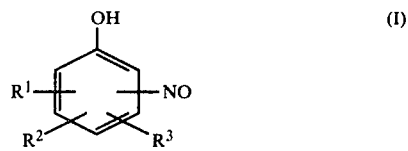

wherein $R^1$, $R^2$ and $R^3$ independently represent hydrogen, a lower alkyl radical, halogen, a carboxyl or sulfo group or the corresponding alkali metal salt thereof or $R^1$, $R^2$ or $R^3$ individually represent an optionally substituted aromatic ring formed by linking two adjacent radicals, with hydrazine, the improvement which comprises employing said aromatic nitroso compound and hydrazine in approximately equivalent stoichiometric amounts in an aqueous medium at temperatures from 10° to 50° C., in the absence of a catalyst, the aromatic nitroso compound being initially introduced into a reaction chamber and the hydrazine being added thereto.

2. A process according to claim 1 wherein the hydrazine is employed in an amount of 1.0 to 1.3 mols per mol of aromatic nitroso compound.

3. A process according to claim 1 wherein the aromatic nitroso compound is 1-nitroso-2-hydroxy-naphthalene-4-sulfonic acid, 1-nitroso-2-hydroxy-naphthalene-6-sulfonic acid, 2-nitroso-1-hydroxy-naphthalene-4-sulfonic acid, 1-nitroso-2-hydroxy-naphthalene-3,6-disulfonic acid, 1-nitroso-2-hydroxy-naphthalene, 1-nitroso-4-hydroxy-naphthalene, 2-nitroso-1-hydroxy-naphthalene, 1-nitroso-2-hydroxy-benzene, 1-nitroso-4-hydroxy-benzene, 1-nitroso-2-hydroxy-benzene-5-sulfonic acid, 1-nitroso-4-hydroxy-benzene-3-sulfonic acid, 1-nitroso-4-hydroxy-benzene-3-carboxylic acid or an alkali metal salt thereof.

4. A process according to claim 1 wherein the hydrazine is employed in the form of hydrazine hydrate.

5. A process according to claim 1 wherein the hydrazine is present in the form of an aqueous solution containing 10 to 90 percent by weight hydrazine.

6. A process according to claim 1 wherein the reaction is carried out at a temperature of 20° to 40° C.

7. A process according to claim 1 wherein the reaction is carried out in a reaction medium whose pH ranges from 4 to 14.

8. A process according to claim 1 wherein the nitroso compound is dissolved or suspended in water after adjusting the pH value to 8 to 12 and thereafter a 20 to 40 percent aqueous solution of hydrazine hydrate is metered in to the reaction chamber containing the nitroso compound at a rate corresponding to the rate of reaction, the temperature being maintained in the range of from 20° to 40° C.

* * * * *